(12) United States Patent
Karstens et al.

(10) Patent No.: US 6,348,590 B1
(45) Date of Patent: *Feb. 19, 2002

(54) METHOD FOR IMPROVING THE EXPLOITABILITY AND PROCESSABILITY OF GUAR ENDOSPERM AND PRODUCTS OBTAINED USING SAID METHOD

(75) Inventors: Ties Karstens, Bötzingen; Armin Stein, Kenzingen, both of (DE)

(73) Assignee: Rhodia Acetow AG, Freiburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/297,227

(22) PCT Filed: Dec. 22, 1997

(86) PCT No.: PCT/EP97/07230

§ 371 Date: May 28, 1999

§ 102(e) Date: May 28, 1999

(87) PCT Pub. No.: WO98/28337

PCT Pub. Date: Jul. 2, 1998

(30) Foreign Application Priority Data

Dec. 23, 1996 (DE) .......................... 196 54 251

(51) Int. Cl.⁷ ............................ C08B 37/00; C07H 1/00
(52) U.S. Cl. .................... 536/114; 536/123.1; 536/124; 536/127; 536/128
(58) Field of Search .............................. 536/114, 123.1, 536/124, 127, 128

(56) References Cited

U.S. PATENT DOCUMENTS

| | | | |
|---|---|---|---|
| 2,496,670 A | * 2/1950 | Moe | 260/209 |
| 5,171,592 A | 12/1992 | Holtzapple et al. | 426/69 |
| 5,473,061 A | * 12/1995 | Brederick et al. | 536/59 |
| 5,489,674 A | 2/1996 | Yeh | 356/114 |
| 5,939,544 A | * 8/1999 | Karstens et al. | 536/124 |

FOREIGN PATENT DOCUMENTS

| | | |
|---|---|---|
| DE | 1 261 384 | 2/1968 |
| DE | 24 41 012 | 3/1975 |
| DE | 33 31 701 | 3/1985 |
| DE | 196 11 416 A1 * | 9/1995 |
| EP | 0 048 612 | 3/1982 |

OTHER PUBLICATIONS

The Oligosaccharides. ed. by Stanek et al., Academic Press, pp. 146–147, 1965.*

Kennedy, John F. "Carbohydrate Chemistry", Clarendon Press, p. 231–232 (Reference is Attached to Office Action), 1988.*

Maier, H., et al,"Guar, Locust Bean, Tara and Fenugreek Gums" Chap.8 pp. 181–226, 1993.

* cited by examiner

Primary Examiner—Ralph Gitomer
Assistant Examiner—Devesh Khare
(74) Attorney, Agent, or Firm—Darby & Darby

(57) ABSTRACT

A method for processing guar endosperm in which guar splits are brought into contact with an amount of liquid ammonia at least sufficient to wet the guar splits at a pressure higher than atmospheric pressure and at a temperature of at least 25° C. The remaining available guar split/liquid ammonia system volume is increased in an explosion like manner by reducing the pressure by at least about 5 bars resulting in the sheaths of the guar splits being torn open to result in a product that can be processed more easily, such as by grinding.

14 Claims, No Drawings

METHOD FOR IMPROVING THE EXPLOITABILITY AND PROCESSABILITY OF GUAR ENDOSPERM AND PRODUCTS OBTAINED USING SAID METHOD

The invention relates to a method for improving the exploitability and processability of guar endosperm and products obtained using said method in the form of ammonia-exploded guar endosperm halves (guar splits), guar flour and guaran powder.

Guar flour is used in the food industry as a stabilizer for ice cream and sherbet and some soft cheeses, as a binder and thickening agent for sauces and similar products as well as also in the cosmetic industry. In industry, guar flour is used for finishing and sizing textiles and as a thickening agent for textile printing pastes. A large amount of guar flour is also used in the paper industry as a beater additive for producing stronger papers.

The main constituent of guar flour is guaran. Guaran is a galactomannan, which consists of approximately 36% D-galactose and 64% mannose. The mannose units are linked together in pyranose form β-1,4 glycosidically into long main chains, to which the galactose units are fixed in pyranose form by α-1,6 glycosidic bonds. In the case of guaran, each second mannose building block of the main chain carries a galactose side group. The average molecular weight of guaran is significantly greater than 200,000.

Guaran is contained in the endosperm of the seed of the guar bean, Cyamopsis tetragonoloba, which is widespread in India and has been cultivated since 1944 on a larger scale in the USA. The endosperm is a food store for the development of the embryo during germination. Because guar is a dicotyledonous plant, there are two endosperm halves in each seed. These endosperm halves surround the embryo and, in turn, are surrounded by a seed coat, which usually has a light brown color. The endosperm itself consists of a layer of cells, the aleuron, and of a nutrient and reservoir substance for the embryo, namely the guaran. The cells of the aleuronic layer contain many aleuron grains, that is, the thickened protein vacuoles. During the germination of the guar seeds, enzymes are synthesized in the aleuron cells and delivered to the endosperm, in order to mobilize reserve materials. The two predominant enzyme activities are α-galactosidase and β-mannase activities.

The seed coat and the embryo are removed industrially by milling steps and mechanical sorting. The different hardness of the seed components is used for this purpose. The multi-step milling and screening steps are frequently combined with other mechanical treatments for breaking open the seeds and sorting the components. There are different types of mills, which can be used in conjunction with roasting processes or the treatment of the seed with water or acid. If used for foods, special attention must be paid to the thorough removal of the embryo. The purified endosperm is sold under the name of "guar splits".

Guar splits usually are ground into a powder, which is called guar flour or guar gum powder. The protein-containing endosperm sheath of the guar splits usually is not removed during the milling. For certain applications, the protein portion in the guar flour, introduced by the protein-containing sheath, interferes. There is therefore a need for a simple and efficient method, with which guaran can be isolated in very pure form from the guar splits.

The milling of the guar splits is, moreover, associated with the expenditure of appreciable electrical energy. The milling conditions furthermore affect the viscosity of the aqueous solution of guaran or its derivatives. There is therefore a need for a method, for which milling of guar splits is not required.

Aqueous solutions of conventional commercial guar flour usually are cloudy. The cloudiness is caused mainly by the presence of insoluble portions of the endosperm. Derivatives, produced from guar flour, admittedly generally show an improved solubility and clarity of the solution. The improved clarity is due to the derivatization and solubilization of insoluble seed impurities. For certain applications, however, the properties of derivatized guar flour are also inadequate. For example, carboxymethylated guar has a relatively high intrinsic viscosity with only a weakly pronounced Newtonian range at low shear rates. When carboxymethylated guar is used as a thickening agent in textile printing, the removability by washing from conventional commercial products is poor. The cause presumably lies in an inhomogeneous distribution of substituents which, in turn, is due to the fact that the derivatizations were carried out on the milled guar splits in a heterogeneous reaction. This disadvantage cannot be eliminated completely even by milling to a very small particle size. There is therefore a need for a guar product, which is completely water soluble or can be derivatized in a homogeneous reaction.

It is therefore an object of the invention to submit proposals, with which the requirements, addressed above, can be satisfied. In particular, the exploitability and processability of guar endosperm halves (guar splits) shall be improved, as shall the millability to guar flour. Moreover, it shall be possible to isolate pure guaran easily and efficiently from guar splits, milling of the guar splits not being required and the guaran being completely water soluble. Moreover, it shall be possible to derivatize the guaran by means of a homogeneous reaction.

Pursuant to the invention, this objective is accomplished by a method for improving the exploitability and processability of guar endosperm, for which the guar endosperm halves (guar splits) are brought into contact with liquid ammonia at an initial pressure, which is higher than atmosphere pressure, and at a temperature of at least 25° C., the amount of liquid ammonia being sufficient at least to wet the surface of the guar endosperm halves and the capacity, available to the system comprising endosperm halves and liquid ammonia, being enlarged explosively with a reduction in pressure by at least about 5 bar and the sheath of the endosperm halves being torn open by these means.

The WO 96/30411 discloses a method for activating polysaccharides by an ammonia explosion. In one example, guar flour is treated with liquid ammonia and exploded. The use of guar endosperm halves instead of guar flour as a starting material is not made obvious by the WO 96/30411.

Preferably, the guar endosperm starting material consists of endosperm halves, which have not been significantly comminuted previously, that is, which essentially are intact guar splits.

During the treatment of the guar splits with liquid ammonia, the liquid ammonia can penetrate the sheath surrounding the guar splits and penetrate into the polysaccharide core. During the subsequent explosion, the volume of the penetrated ammonia increases suddenly. The gaseous ammonia can no longer escape quickly enough through the sheath and leads to a tearing open of the surface of the guar splits. The guaran, contained in the native guar splits, is microcrystalline and generally has a degree of crystallinity of about 20 to 30%. Under the action of the liquid ammonia, there is at least partial swelling of the polysaccharide substance. Intermolecular hydrogen bonds between the molecular chains are broken, since the ammonia molecule competes with the hydroxyl groups of the neighboring molecules. As a result of the explosion, there is evaporation of the ammonia between the chains of molecules. The chains of molecules, the intermolecular hydrogen bonds of which have previously been broken, are torn apart. This leads to an exposure of regions, which normally are not readily accessible to reagents. In particular, the polysaccharide portion becomes water soluble due to the ammonia explosion. The guaran in the exploded guar splits no longer is crystalline and, instead, has become amorphous.

When there is mention of "explosive" in connection with the inventive method, then this concept is to be interpreted narrowly. Preferably, the explosive increase in volume takes place within a period of less than 1 second and, in particular, of the less than 0.5 seconds. The ammonia explosion of the inventive method can take place batchwise or continuously. If the process is carried out continuously, the consideration is tailored to an incremental amount of endosperm halves and liquid ammonia. Preferably, the guar endosperm halves and the liquid ammonia are brought into contact in pressure equipment and the pressure on the system of a endosperm halves and liquid ammonia is relieved by transfer to an explosion space, which has a capacity larger than that of the pressure equipment. Preferably, the initial pressure is between about 5 and 46 bar and especially between about 25 and 30 bar. The minimum pressure drop of 5 bar is critical. If it is not reached, the objective of the invention is not attained. No further advantages are achieved if the upper limiting value of about 46 bar is exceeded. Adjusting the pressure to such a high value is associated with a relatively large expenditure for equipment, so that a further increase in pressure is not meaningful from practical considerations. A temperature of about 25° to 85° C. or 55° to 65° C. respectively correlates with these pressure limits given. Preferably, the initial pressure in the system of guar endosperm halves and liquid ammonia is lowered explosively by at least about 10 bar and especially by about 30 bar. Preferably, the explosion takes place in an explosion space, which is kept under a vacuum.

A sufficient amount of ammonia must be forced into the pressure equipment, so that liquid ammonia is present under the conditions of pressure and temperature required pursuant to the invention and so that at least the surface of the guar endosperm halves is wetted. Preferably, for each part by weight of guar endosperm halves, there is at least about 1 part by weight of liquid ammonia and especially at least about 2 parts by weight and particularly about 5 to 10 parts by weight of liquid ammonia.

The ammonia explosion step of the inventive method can be carried out discontinuously or continuously. For the discontinuous method, the apparatus essentially has a pressure vessel, which can be filled with the material that is to be treated, and a collection and expansion vessel, which can be connected to the pressure vessel by way of a valve. It should be noted in this connection that the valve, in the open state, has a large clear opening, so that the guar endosperm halves do not back up during the explosion process, leaving the ammonia as the only material to escape. The capacity of the explosion vessel is a multiple of that of the pressure vessel. For example, the capacity of the pressure vessel is 1 L and the capacity of the explosion vessel 30 L. The pressure vessel is connected with a pipeline supplying ammonia, in which optionally a pressure-increasing mechanism is connected. In addition, to increase the pressure further, a pipeline for supplying inert gases, such as nitrogen, may be provided.

The method can be carried out continuously using a tubular or cylindrical, pressure-resistant reactor, in which the guar endosperm halves are brought into contact with the liquid ammonia in the cylinder of the reactor and the impregnated material is transported as a plug through the reactor with the help of a screw conveyor and discharged intermittently through a valve or a suitable system of pressure locks into a collection space.

The contact time between the liquid ammonia and the guar endosperm halves is not critical. Preferably, it is at least 1 minute and usually it is 4 to 8 minutes or longer. After the explosion, the material obtained generally contains less than about 2 percent by weight of ammonia. The residual ammonia content is not critical for the further method.

In an advantageous further development of the inventive method, the (ammonia-) exploded material is treated with an extraction agent, so that the guaran essentially goes into solution and the endosperm sheaths essentially remain undissolved, the endosperm sheaths are separated and guaran optionally is recovered from the guaran solution.

Preferred extraction agents for the treatment of the ammonia-exploded material are aqueous media, especially water, or other solvents with comparable dissolving properties. During the extraction of the ammonia-exploded material with, for example, water, the polysaccharide portion of the guar splits is dissolved readily, while the sheath, surrounding the splits, remains undissolved and can be removed by the usual techniques, for example, by filtration or centrifugation. The exploded material is treated with the extraction agent preferably at a temperature of about 25° to 95° C.

The aqueous guaran solution can be used as such, for example, for making derivatives in a homogeneous, aqueous phase or dried by the usual methods. Spray drying or drum drying are particularly suitable for the drying process. The powder obtained has outstanding solubility in water with formation of very clear solutions.

According to the inventive method, guaran is obtained as an aqueous solution or as a powder with outstanding water solubility, so that no further derivatization is required to bring about water solubility. If required in a particular case, derivatization of guaran, produced pursuant to the invention, leads to products with surprisingly improved properties, since more homogeneous derivatization products are obtained due to the improved accessibility for the reagents producing the derivatives. The derivatives can be produced using less chemicals and obtaining fewer by-products. At the same time, the homogeneity of the distribution of the substituents is greater. The inventive method does not result in any decrease in the DP of the guaran worth noting. It was possible to show by X-ray spectra that the guaran, which originally was at least partially crystalline, is now amorphous. The molecular weight is clearly less than that of the native starting material. The molecular weight boundaries for the guaran, obtained pursuant to the invention by extraction from the ammonia-exploded guar splits, are set at about 1.5 to 2.5 million and especially at about 1.8 to 2.2 million. The proportion of water-soluble fraction in the guar splits, ammonia-exploded pursuant to the invention, ranges from about 53 to 59% by weight and especially from 56 to 66% by weight. If the ammonia-exploded guar splits, obtained pursuant to the invention, are subjected to conventional milling to a particle size of a little more than about 100 $\mu$m, then this leads to a further decrease in the molecular weight of the guaran in the milled material. Molecular weights of about 1.4 to about 1.65 million are obtained here, while the water-soluble portion is about 65 to 77% by weight. Finally, if the guar splits are dried and then milled to a particle size of about 100 $\mu$m, then the molecular weight of the guaran is lowered particularly extensively. In these cases, the molecular weight of the guaran is between about 450,000 and 900,000, the water-soluble portion being between about 71 and 85% by weight.

The guar splits, obtained pursuant to the invention and exploded with ammonia, can furthermore be characterized as follows. They have sheaths, which are torn open by the ammonia explosion. These sheaths essentially remain chemically unchanged after the ammonia explosion. The guaran, contained in the guar splits or recovered therefrom, exhibits increased reactivity in chemical reactions, such as the etherification (carboxymethylation), and especially silylation. The guaran, still enclosed, is porous and amorphous. The porosity can be described as follows. The ammonia explosion of the guar splits creates vacuoles (hollow spaces) in the interior of the splits which, due to the gaseous ammonia escaping, are connected with the surface over ducts. In the swollen state, the splits have swollen to three times their volume. The porosity can be confirmed by scanning electron microscope photographs. In this connection, reference is made to the attached scanning electron microscope photographs. The molecular weight falls within the boundaries given above. The water-soluble portion, attributed essentially to the guaran, also falls within the limits given above. Moreover, it has been observed that the swellability of the ammonia-exploded guar splits increases greatly above that of the not-exploded native materials. This is true for very different media, such as water or a mixture of "water and sodium carbonate" at room temperature or at elevated temperatures. For measurements at a temperature of 23° C. in an aqueous medium, it has turned out that, after a swelling time of 60 minutes, the guar splits, obtained pursuant to the invention, swell almost 100% more than do native comparison products. For a specified swelling volume, this means that this volume is attained in half the time by guar splits obtained pursuant to the invention. If, in isolated cases, with respect to particular uses of the guaran, the drying for removing residual ammonia is inadequate, then this residual ammonia can be removed further and sufficiently by an exchange with, for example, isopropanol. Furthermore, it has been observed that the ammonia-exploded guar splits have a smaller proportion of volatile materials than do the comparison splits. Moreover, the clarity of the solution of the ammonia-exploded guar splits is slightly higher than that of the comparison splits. This improved transparency leads to the assumption that the ammonia-exploded splits contain less water-insoluble material.

A further development of the inventive method consists therein that the exploded guar splits, obtained by the ammonia explosion utilized pursuant to the invention, are milled in the usual manner to guar flour. In this connection, it is generally preferred that water be added during the milling process. If in a particular case, water is not to be present during the milling, then the milling advisably is preceded by a drying step.

The invention will now be explained in greater detail by the following examples

EXAMPLE 1

Conventional, commercial guar splits (300 g) are added to a 1 liter autoclave with a double wall for steam heating. Subsequently, 500 g of liquid ammonia were forced into the autoclave over a valve. By the additional steam heating of the autoclave, the temperature was raised to 66° C., the pressure within the autoclave increasing to about 20 bar. The system was maintained for 60 seconds under these conditions. Subsequently, by opening a valve (with an opening having a diameter of 4 cm), the pressure was reduced suddenly and completely in a collection vessel having a capacity of 30 liters. The ammonia content of the product obtained in the collection vessel was about 0.8% by weight, base on the guar.

EXAMPLE 2

Ammonia-exploded guar splits (8 g) were brought into a heated jacketed vessel, which contained 192 g of water at a temperature of 50° C. The vessel was equipped with a stirrer (Heidolph RZR2101 electronic drive), which made it possible to follow the torque of the stirred mass. The stirrer used was a surface stirrer, which was operated at 250 rpm. The course of the torque corresponds to the resistance exerted by the aqueous solution on the stirrer and, with that, to the viscosity of the aqueous solution. The viscosity depends on the amount of guaran dissolved and increases as the concentration of this biopolymer increases. After 2½ hours, the course of the torque reaches a plateau. It can be concluded from this that the dissolving process has ended. During visual observation, undissolved particles (endosperm sheaths) can be recognized, which fall to the bottom of the vessel when the stirrer is switched off. The supernatant solution is clear and can be decanted off.

In comparison experiments, untreated guar splits (a commercial version) were stirred in water under the same conditions and the course of the torque was followed. Furthermore, untreated splits were stirred in a 4% ammonium hydroxide solution at 25° C. During the comparison experiments, there was no increase in viscosity worth mentioning. This indicates that guaran was not dissolved from the untreated guar splits.

Further determinations reveal the following. By gel chromatographic analysis, it was noted that the ammonia-exploded guar splits contained guaran having a molecular weight of 1,996,000 and a water-soluble portion of 61% by weight. The corresponding values for the comparison splits were a molecular weight of 278,900 and a water-soluble portion of 51% by weight.

EXAMPLE 3

The effect of milling and, optionally, of the prior drying on the molecular weight of the guaran in the guaran flour obtained, as well as on the proportion of the water-soluble fraction, are determined here. The native guar splits, as well as the ammonia-exploded guar splits of Example 2, were therefore used. In one case, milling was carried out only to an average particle diameter of more than 100 μm. This was done in a so-called cryo mill under gentle conditions and with the addition of liquid nitrogen. Moreover, an experiment was conducted, in which the milling was carried out to an average particle diameter of about 100 μm, the material being dried in a vacuum drying oven overnight at a temperature of 40° C. The data, given in the Table below, was then obtained.

TABLE

|  | Native Guar Splits | | Ammonia-Treated Guar Splits | |
| --- | --- | --- | --- | --- |
|  | Molecular weight | Water-soluble fraction | Molecular weight | Water-soluble fraction |
| Guar splits | 2,789,000 | 51% | 1,996,000 | 61% |
| Guar splits after milling[1)] | 1,720,000 | 60% | 1,510,000 | 71% |

TABLE-continued

|  | Native Guar Splits | | Ammonia-Treated Guar Splits | |
| --- | --- | --- | --- | --- |
|  | Molecular weight | Water-soluble fraction | Molecular weight | Water-soluble fraction |
| Guar splits after drying and milling[2] | 1,129,000 | 66% | 577,400 | 78% |

Comments:
[1]Gentle cryo milling, with addition of liquid nitrogen, to a particle diameter greater than 100 μm.
[2]Initially, material is dried overnight at 40° C. under a vacuum. This is followed by gentle cryo milling with addition of liquid nitrogen to an average particle size of 100 μm.

Comments

What is claimed is:

1. A method for processing of guar endosperm to isolate the galactomannan of D-galactose and mannose component (guaran) therefrom, comprising:
providing guar endosperm halves;
bringing the halves into contact with liquid ammonia at an initial pressure, higher than atmospheric pressure, and at a temperature of at least 25° C., the amount of liquid ammonia being sufficient at least for wetting the surface of the guar endosperm halves; and
increasing the volume available to the system of guar endosperm halves and liquid ammonia explosively by lowering the pressure by at least about 0.5 Mpa (5 bar) to tear open the sheaths of the guar endosperm halves to isolate the guaran.

2. The method of claim 1, wherein the explosive increase in volume is carried out within a time of less than 1 second.

3. The method of claim 1, wherein the guar endosperm halves and the liquid ammonia are brought into contact in pressure equipment and the pressure on the system of guar endosperm halves and liquid ammonia is reduced by transfer into an explosion space having a capacity larger than that of the pressure equipment.

4. The method of claim 1, wherein the initial pressure is adjusted to a value between about 0.5 and 4.6 MPa (5 and 46 bar).

5. The method of claim 3, wherein the temperature in the pressure equipment is adjusted before the explosive increase in volume to a value between about 25° and 85° C.

6. The method of claim 1, wherein the initial pressure is lowered by at least about 1 MPa (10 bar).

7. The method of claim 1, wherein at least one part by weight of liquid ammonia is used per part by weight of guar endosperm halves.

8. The method of claim 1, further comprising milling the ammonia-exploded material into guar flour.

9. Ammonia-exploded guar endosperm halves (guar splits), produced by the method of claim 1.

10. The method of claim 1, further comprising treating the exploded material with an extraction agent, so that the guaran goes substantially into solution and the endosperm sheaths remain substantially undissolved, removing the endosperm sheaths and, optionally, recovering the guaran from the guaran solution.

11. The method of claim 10, further comprising using an aqueous extraction agent, especially water.

12. The method of claim 10, wherein the exploded material is treated with the extraction agent at a temperature of about 25° to 95° C.

13. The method of claim 10, further comprising removing the endosperm sheaths by filtration or centrifugation.

14. The method of claim 10, further comprising obtaining the guaran by spray drying.

* * * * *